(12) United States Patent
Yates et al.

(10) Patent No.: US 10,479,739 B2
(45) Date of Patent: Nov. 19, 2019

(54) INTEGRATED SYSTEM FOR OXYGEN RECOVERY FOR DEEP SPACE MISSION

(71) Applicant: HONEYWELL INTERNATIONAL INC., Morris Plains, NJ (US)

(72) Inventors: Stephen Yates, South Barrington, IL (US); Alexander Bershitsky, Northbrook, IL (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 149 days.

(21) Appl. No.: 15/586,537

(22) Filed: May 4, 2017

(65) Prior Publication Data

US 2018/0319660 A1 Nov. 8, 2018

(51) Int. Cl.
| | | |
|---|---|---|
| C01B 3/24 | (2006.01) | |
| C07C 1/12 | (2006.01) | |
| C25B 1/02 | (2006.01) | |
| C25B 1/04 | (2006.01) | |
| C01B 3/56 | (2006.01) | |

(52) U.S. Cl.
CPC .............. $C07C\ 1/12$ (2013.01); $C01B\ 3/56$ (2013.01); $C25B\ 1/04$ (2013.01); $C01B\ 2203/0272$ (2013.01); $C01B\ 2203/0405$ (2013.01); $C01B\ 2203/065$ (2013.01); $C01B\ 2203/1241$ (2013.01); $C01B\ 2203/145$ (2013.01)

(58) Field of Classification Search
CPC .... C01B 3/24; C07C 1/12; C25B 1/02; C25B 1/04

See application file for complete search history.

(56) References Cited

U.S. PATENT DOCUMENTS

| | | |
|---|---|---|
| 2,471,398 A | 5/1949 | Simpson et al. |
| 2,555,210 A | 5/1951 | Waddill et al. |
| 2,647,041 A | 7/1953 | Robinson |
| 2,656,306 A | 10/1953 | Bergstrom et al. |
| 3,079,237 A | 2/1963 | Taylor |

(Continued)

OTHER PUBLICATIONS

Christian Junaedi et al., "Compact and Lightweight Sabatier Reactor for Carbon Dioxide Reduction", 41st International Conference on Environmental Systems, American Institute of Aeronautics and Astronautics, 2011.

(Continued)

*Primary Examiner* — Kevin Joyner
(74) *Attorney, Agent, or Firm* — Shimokaji IP (57) ABSTRACT

An environmental control system includes a carbon dioxide source; a compressor downstream of the carbon dioxide source; a Sabatier reactor downstream of the compressor, wherein the Sabatier reactor reacts carbon dioxide with hydrogen to produce methane and water; a water separator downstream of the Sabatier reactor, wherein the water separator separates hydrocarbons from water, wherein the hydrocarbons include methane; a pyrolysis assembly downstream of the water separator and upstream of the compressor, wherein the pyrolysis assembly pyrolyzes methane to produce carbon and hydrogen, wherein the pyrolysis assembly includes a pre-form that adheres carbon; and an oxygen generating assembly (OGA) downstream of the water separator and upstream of the compressor, wherein the OGA converts water to hydrogen and oxygen.

19 Claims, 9 Drawing Sheets

(56) References Cited

U.S. PATENT DOCUMENTS

| | | |
|---|---|---|
| 3,138,434 A | 6/1964 | Diefendorf |
| 3,340,012 A | 9/1967 | Moehl |
| 3,399,969 A | 9/1968 | Bokros et al. |
| 3,488,401 A | 1/1970 | Ames |
| 3,799,866 A | 3/1974 | Lengemann |
| 3,851,048 A | 11/1974 | Araki et al. |
| 4,410,504 A | 10/1983 | Galasso et al. |
| 4,452,676 A | 6/1984 | Birbara et al. |
| 4,770,867 A | 9/1988 | Coulon et al. |
| 5,061,455 A | 10/1991 | Brose et al. |
| 5,362,373 A | 11/1994 | Murdoch et al. |
| 5,418,063 A * | 5/1995 | Booth .................... C04B 35/83 427/113 |
| 6,221,475 B1 | 4/2001 | Domergue et al. |
| 8,945,351 B2 | 2/2015 | Bratina et al. |
| 2004/0112741 A1 | 6/2004 | Murdoch |
| 2012/0259025 A1 | 10/2012 | Zhao |
| 2015/0010452 A1 | 1/2015 | Elliott et al. |
| 2015/0147259 A1 | 5/2015 | Noyes |
| 2016/0016794 A1 | 1/2016 | Noyes |
| 2016/0017800 A1 | 1/2016 | Simpson |
| 2016/0083658 A1 | 3/2016 | Sanner |
| 2016/0230311 A1 | 8/2016 | Vince |
| 2017/0239609 A1 * | 8/2017 | Luisman ............ B01D 53/0423 |

OTHER PUBLICATIONS

P. K. Sharma et al., "Methane Pyrolysis and Disposing Off Resulting Carbon", In Situ Resource Utilization (ISRU 3) Technical Interchange Meeting: Abstracts; 31-32, 1999.

Robert J. Erickson et al., "International Space Station United States Orbital Segment Oxygen Generation System On-orbit Operational Experience," SAE Int. J. Aerosp. 1(1):15-24, 2009.

Kevin C. Takada et al., "Advancing the Oxygen Generation Assembly Design to Increase Reliability and Reduce Costs for a Future Long Duration Mission", 45th International Conference on Environmental Systems, Texas Tech University, 2015.

* cited by examiner

INTEGRATED SYSTEM FOR OXYGEN RECOVERY FOR DEEP SPACE MISSION

BACKGROUND OF THE INVENTION

The present invention generally relates to oxygen recovery and, more particularly, to apparatus and methods of oxygen recovery in closed environments.

In long duration manned missions to Mars, the Moon, asteroids, etc. carrying sufficient oxygen to provide for the needs of the crew is a critical obstacle. NASA believes that the only solution is a "closed loop" in which the carbon dioxide exhaled by crew members is chemically converted back to oxygen. This has been a NASA goal for a number of years, but an effective solution to the problem has not been discovered.

Current processes that are well known to those skilled in the art, and which are in use on the International Space Station (ISS) include the Carbon Dioxide Removal Assembly (CDRA) which recovers carbon dioxide from the atmosphere in the cabin, and the Oxygen Generation Assembly (OGA) which uses electrolysis of water to generate hydrogen and oxygen. A developmental Sabatier reactor is in evaluation on the ISS which uses the hydrogen from the OGA to reduce the carbon dioxide from the CDRA to methane and water. The water can then be sent to the OGA to make oxygen.

However, only 50% of the CO2 can be reduced, because the Sabatier reaction requires 4 moles of hydrogen, while the OGA reaction only generates 2 moles. This limits oxygen recovery to <50%. The hydrogen "wasted" in making methane must be recovered. Methane pyrolysis can be of limited use. Others have tried to accomplish methane pyrolysis using microwaves, among other techniques, but they generate mostly acetylene, rather than carbon, so the maximum possible hydrogen recovery is reduced.

Acetylene is both flammable and explosive. Generation of this gas requires that it be promptly vented for safety reasons. The quantities generated by these other technologies are significant, meaning that a significant gap in loop closure will be involved. Some prior processes generate carbon via either the Bosch or Boudouard reactions. However, because these reactions are catalytic, and the carbon accumulates on and fouls the catalyst, they must be cleaned periodically, generating carbon dust. Other processes directly generate carbon soot.

Dust and soot are particularly difficult to deal with in a zero gravity environment since they can foul or escape from filters, and because they represent both an inhalation hazard to people and a threat to equipment. Uncontrolled soot generation can clog reactors and tubes. Even if soot or dust is vented from the spacecraft, it can be damaging. Soot in the vicinity of the spacecraft may coat solar panels or other exterior structures. In a Mars habitat scenario, discharging soot may contaminate the environment near the habitat, interfering with experimentation or affecting the operation of other equipment.

As can be seen, there is a need for improved apparatus and methods to recover oxygen in closed and/or gravity-free environments such as deep space vehicles.

SUMMARY OF THE INVENTION

In one aspect of the present invention, an environmental control system comprises a carbon dioxide source; a compressor downstream of the carbon dioxide source; a Sabatier reactor downstream of the compressor, wherein the Sabatier reactor produces methane and water; a water separator downstream of the Sabatier reactor, wherein the water separator produces methane and water; a pyrolysis assembly downstream of the water separator and upstream of the compressor, wherein the pyrolysis assembly includes a pre-form that adheres carbon, wherein the pyrolysis assembly produces hydrogen; and an oxygen generating assembly (OGA) downstream of the water separator and upstream of the compressor, wherein the OGA produces hydrogen and oxygen.

In another aspect of the present invention, an environmental control system comprises a carbon dioxide source; a compressor downstream of the carbon dioxide source; a Sabatier reactor downstream of the compressor, wherein the Sabatier reactor reacts carbon dioxide with hydrogen; a water separator downstream of the Sabatier reactor, wherein the water separator separates hydrocarbons from water, wherein the hydrocarbons include methane and ethane; a pyrolysis assembly downstream of the water separator and upstream of the compressor, wherein the pyrolysis assembly includes a pre-form that adheres carbon, wherein the pyrolysis assembly pyrolyzes methane; and an oxygen generating assembly (OGA) downstream of the water separator and upstream of the compressor, wherein the OGA electrolyzes water.

In a further aspect of the present invention, an environmental control system comprises a carbon dioxide source; a compressor downstream of the carbon dioxide source; a Sabatier reactor downstream of the compressor, wherein the Sabatier reactor reacts carbon dioxide with hydrogen to produce methane and water; a water separator downstream of the Sabatier reactor, wherein the water separator separates hydrocarbons from water, wherein the hydrocarbons include methane; a pyrolysis assembly downstream of the water separator and upstream of the compressor, wherein the pyrolysis assembly pyrolyzes methane to produce carbon and hydrogen, wherein the pyrolysis assembly includes a pre-form that adheres carbon; and an oxygen generating assembly (OGA) downstream of the water separator and upstream of the compressor, wherein the OGA electrolyzes water to hydrogen and oxygen.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, the present invention can be integrated into environments such as spacecraft used in long-duration missions, specifically, space stations and spacecraft and habitats used in and beyond low earth orbit, as the invention can operate independent of gravity. The present invention may also be used for aircraft, as another example, where its gravity independence would help mitigate failures due to managing liquids under turbulence.

The present invention may be an environmental control system, such as an Environmental Control and Life Support System (ECLSS). A methane pyrolysis reactor can be combined with a Sabatier reactor and an Oxygen Generating System (OGA) in such a way that the net result is more than the sum of the parts. The reduction of carbon dioxide to recover oxygen requires hydrogen, which can be provided by the OGA. The OGA may not provide enough hydrogen to reduce all of the CO2, given the Sabatier chemical reaction, which produces methane and water. As a result, oxygen can only be recovered from half the $CO_2$. However, the present invention can recover hydrogen from the produced methane via pyrolysis, restoring the required balance between carbon dioxide and hydrogen. By restoring this balance, the theoretical oxygen recovery, based on stoichiometry, is 100%:

Sabatier: $CO_2 + 4H_2 \longrightarrow CH_4 + 2H_2O$

Electrolysis: $2H_2O \longrightarrow 2H_2 + O_2$

Pyrolysis: $CH_4 \xrightarrow{\Delta} 2H_2 + C$

Net reaction: $CO_2 \longrightarrow O_2 + C$

An environmental control system employing a Sabatier reactor, OGA, and pyrolysis reactor are described in US patent application entitled "Inductively Heated Methane Pyrolysis Reactor for Advanced Oxygen Recovery in Environmental Control and Life Support Systems", concurrently filed herewith and incorporated herein in its entirety.

In the pyrolysis reactor, a disposable pre-form insert can have a high surface area on which carbon can grow by carbon vapor deposition/infiltration. The presence of this high surface area changes the product distribution to make more carbon and hydrogen, and less of other gas phase hydrocarbons.

Figure 1:
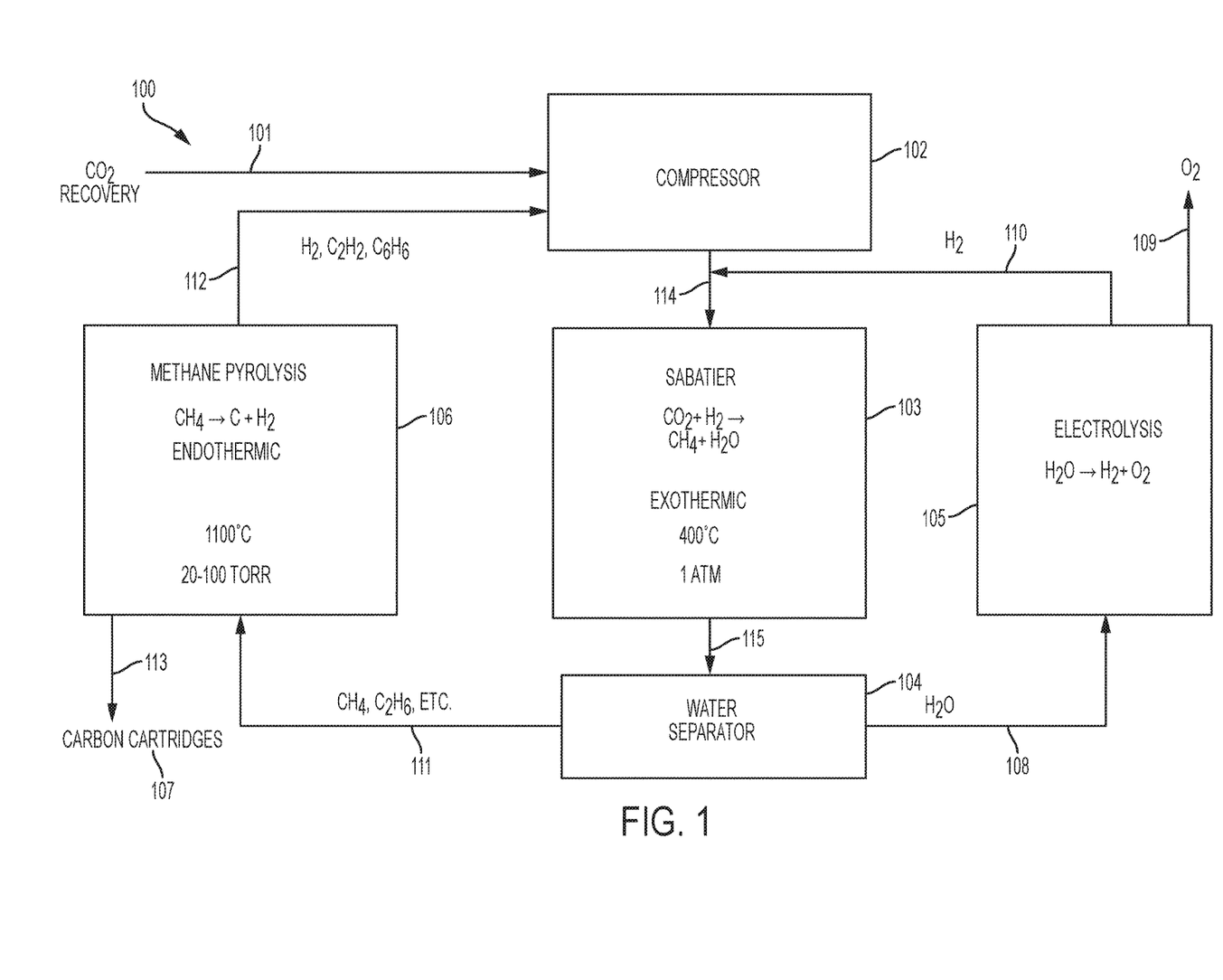
FIG. 1 is a schematic diagram of an environmental control system (ECS) in accordance with an exemplary embodiment of the present invention.

FIG. 1 is a schematic diagram of an exemplary embodiment of an environmental control system (ECS) 100, such as an Environmental Control and Life Support System (ECLSS). The ECS 100 may receive $CO_2$ from a carbon dioxide source 101, for example, a Carbon Dioxide Removal Assembly (CDRA). A compressor 102, downstream of the $CO_2$ source 101, may receive the $CO_2$ from the carbon dioxide source 101. After compression it may be mixed with hydrogen from an Oxygen Generating Assembly (OGA) 105, further described below. This mixture 114 will thus comprise a mixture of $CO_2$ and $H_2$.

In embodiments, the compressed mixture 114 of $CO_2$ and $H_2$ may be at a pressure of about 1 atm. In embodiments, the compressed mixture may be in a mole ratio of about 4 to about 5, $H_2$ to $CO_2$.

A reactor 103, such as a Sabatier reactor, downstream of the compressor 102, may receive and cause the compressed mixture 114 to undergo the following reaction:

Sabatier $CO_2 + 4H_2 \rightarrow CH_4 + 2H_2O$

Sabatier reactors are well known in the art and described, for example, in Junaedi et al., "Compact and Lightweight Sabatier Reactor for Carbon Dioxide Reduction", 41st International Conference on Environmental Systems, 2011, American Institute of Aeronautics and Astronautics, https://ntrs.nasa.gov/archive/nasa/casi.ntrs.nasa.gov/20120016419.pdf, which is incorporated herein in its entirety. The Sabatier reactor 103 may be of conventional design and, in embodiments, operate at about 400° C. and 1 atm in the presence of a catalyst such as nickel or ruthenium. The reaction is exothermic. Thus, heat must be supplied at start up, but after that point, it should instead be cooled. Products 115 exiting the Sabatier reactor 103 include methane and water.

A water extractor 104, downstream of the Sabatier reactor 103, may be in the form of a condenser, in some embodiments. In other embodiments, the water extractor 104 may have a zeolite membrane. Accordingly, the water extractor 104 may produce water 108 separated from hydrocarbons 111. The hydrocarbons 111 may include methane and ethane—$CH_4$ and $C_2H_6$. In embodiments, the methane may be present at greater than about 90% of the hydrocarbons 111.

A methane pyrolysis assembly 106, downstream of the water separator 104, may receive the hydrocarbons 111. In embodiments, a concentration of water entering the pyrolysis assembly 106 is kept low—such as less than about 1%—since, in the presence of water, the thermodynamically preferred product is CO, not carbon.

The pyrolysis assembly 106 may, in embodiments, operate at about 1100°–1200° C., about 20-100 torr. Thus, the pyrolysis assembly 106 may cause methane to be pyrolyzed according to the following reaction:

Pyrolysis: $CH_4 \xrightarrow{\Delta} 2H_2 + C$

Also produced by the pyrolysis assembly 106 may be hydrocarbons such as acetylene and benzene—$C_2H_2$ and $C_6H_6$. In embodiments, the pyrolysis assembly 106 may consume about 1.51 kg/day of methane and produce about 0.38 kg/day of hydrogen at a 100% yield.

Figure 2:
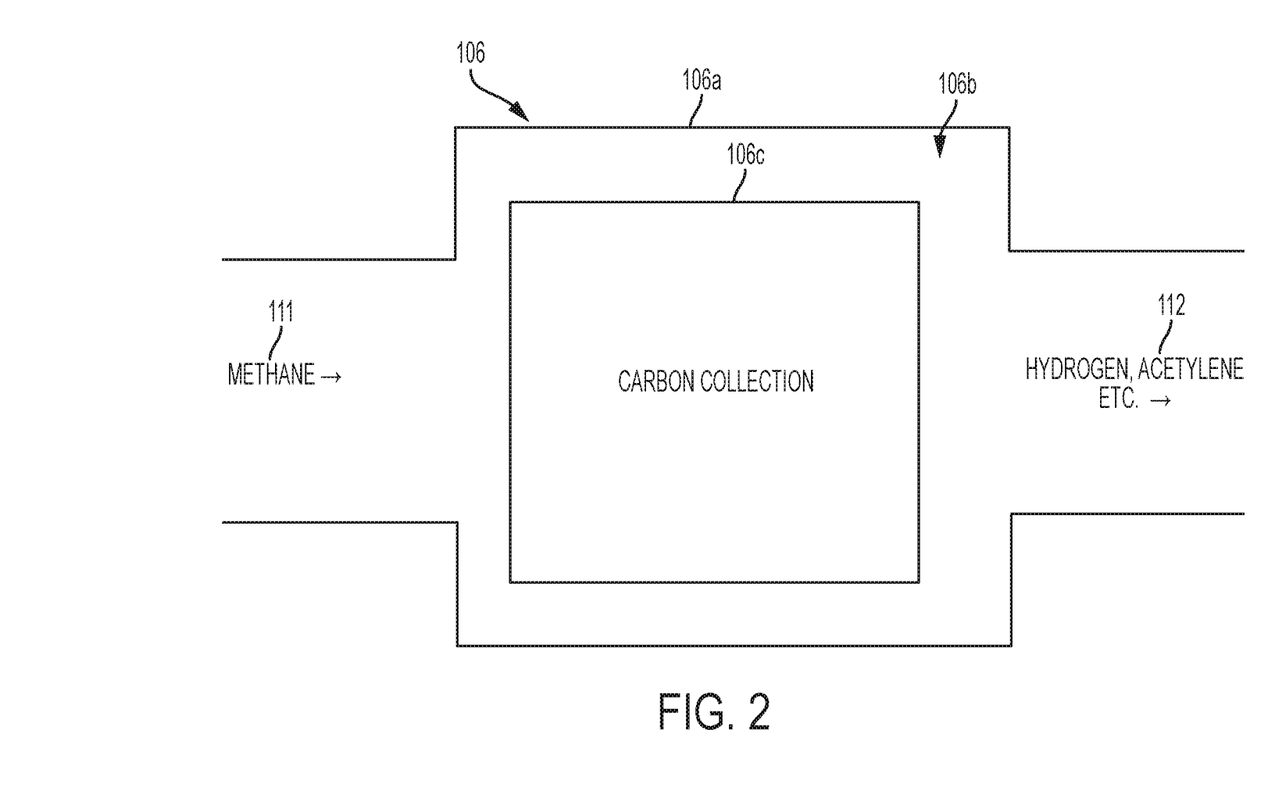
FIG. 2 is a schematic diagram of a pyrolysis assembly of an ECS in accordance with an exemplary embodiment of the present invention.

In FIG. 2A, the pyrolysis assembly 106 may include a housing 106a that forms a chamber 106b, according to embodiments. The chamber 106b may be temperature and/or pressure controlled. One or more pre-forms 106c are inside the chamber 106b and provide a surface area on which carbon, resulting from pyrolysis, can be deposited.

In embodiments, inductive heating of the pre-form 106c is employed. This can focus the heat on the pre-form itself, rather than heating from the outside edges as would be the case with resistive/radiative heating. The pre-form 126 can be composed of a high surface area material, such as a loosely woven or unwoven fabric or highly porous solid. An architecture could prevent clogging of the porous pathways (e.g., by using larger pores near the surface of the pre-form). To be heated by induction heating, the pre-form can be made of a magnetically susceptible material, or it can include a magnetically susceptible material inserted within the pre-form to act as a susceptor and promote heating indirectly. Because only the pre-form 106c is heated, it can be heated rapidly to the required temperature. This can minimize "down time" after change out of pre-forms, as described below. By reducing the size of the heated zone, it also reduces power consumption and heat losses.

Figure 3A:
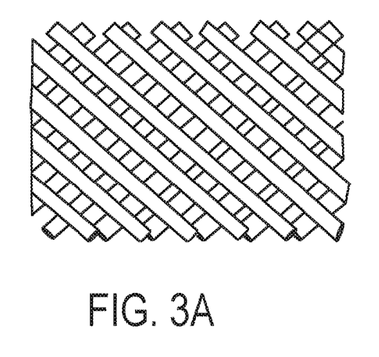
FIGS. 3A-C are alternative embodiments of a pre-form for use in a pyrolysis assembly according to the present invention.

In FIG. 3A, according to an embodiment, a pre-form may be configured with alternating layers of densely packed fibers. In other words, the fibers in one layer extend parallel to one another so that criss-crossed layers of fibers are provided to form a "tight region" of fibers. In embodiments, the fibers can be made of carbon. The fibers in this layer may have a diameter of about 2 to 20 microns. Since the surface of these fibers is the site for carbon vapor deposition, these densely packed regions increase the surface area/volume ratio for the pre-form.

Figure 3B:
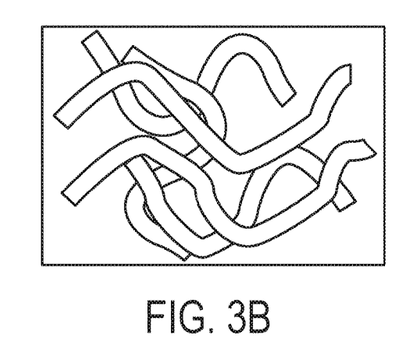

In FIG. 3B, according to an embodiment, a pre-form may be configured with loosely and/or randomly packed fibers. In other words, the fibers may have a "felt-like" structure to form a "loose region" of fibers. In embodiments, the fibers can be made of carbon. These loosely packed regions have a lower surface area/volume ratio, but, because the voids between fibers are larger, they permit more rapid diffusion of gases.

Figure 3C:
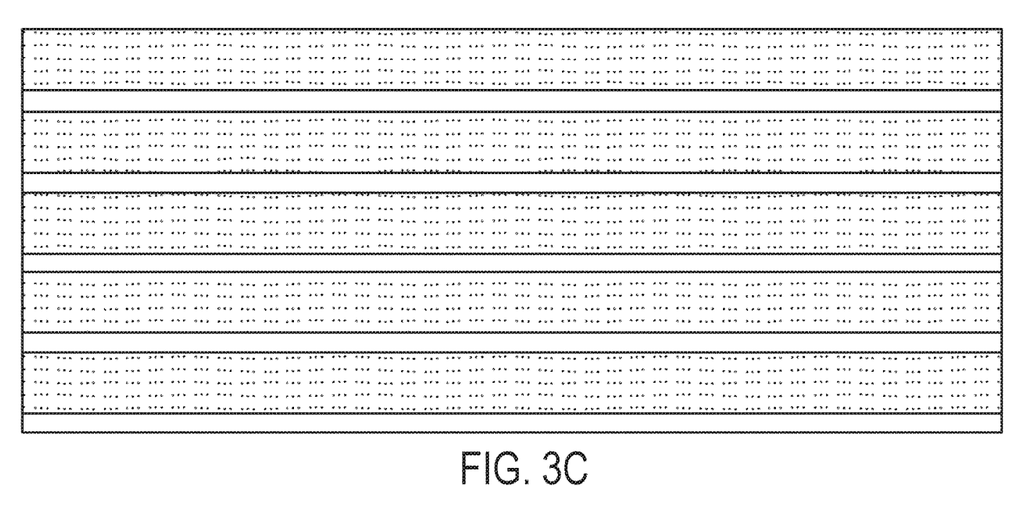

In FIG. 3C, according to an embodiment, a pre-form may be configured with alternating layers of "tight regions" and "loose regions". In this arrangement, the loose regions provide better access to all parts of the tight regions.

To make efficient use of the pre-form, and minimize the consumption of pre-forms during a mission, it is useful to maximize the amount of carbon accumulated on it. In other words, the density of the pre-form after carbon vapor deposition should be as high as possible. Carbon vapor deposition is a surface reaction, so increasing the surface area/volume ratio of the pre-form is important to achieving this goal. It is also important to manage the deposition so that it is even through the part. If deposition occurs only at the outside edge of the pre-form, it will seal the surface, preventing hydrocarbon gases from reaching the interior surfaces. A design for the pre-form in which high surface area regions alternate with more loosely packed regions enabling rapid diffusion allows this to occur.

In embodiments, one or more discarded pre-form(s) 107, such as in the form of a carbon cartridge, may be periodically removed from the pyrolysis assembly 106, upon the pre-form(s) becoming loaded with carbon from pyrolysis.

Referring back to FIG. 1, pyrolysis products 112 may exit the pyrolysis assembly 106 and enter the compressor 102. The pyrolysis products 112 may include $H_2$, $C_2H_2$ and $C_6H_6$. In embodiments, $H_2$ may be present in the pyrolysis products from about 50 to about 90 volume percent.

The Oxygen Generating Assembly (OGA) 105 is upstream of the compressor 102 and downstream of the water separator 108. Accordingly, the OGA 105 may receive $H_2O$ 108 from the water separator 108. In the OGA 105, $H_2O$ may undergo electrolysis according to the following:

The OGA 105 may be of conventional design and, in embodiments, operate at the following condition described, for example in Takada et. al., "Advancing the Oxygen Generation Assembly Design to Increase Reliability and Reduce Costs for a Future Long Duration Mission" 45th International Conference on Environmental Systems, July 2015; Erickson et. al., "International Space Station United States Orbital Segment Oxygen Generation System On-orbit Operational Experience", "International Conference on Environmental Systems (ICES); 30 Jun.-3 Jul. 2008; San Francisco, Calif., SAE Int. J. Aerosp. 1(1):15-24, 2009, both of which are incorporated herein in their entirety. The produced $O_2$ 109 from the OGA 105 may be routed for use by occupants associated with the ECS 100. The produced $H_2$ 110 from the OGA 105 may be routed to the compressor 102.

Taking into account the $H_2$ from the OGA 105 and from the pyrolysis assembly 106, total $H_2$ to total $CO_2$ entering the compressor 102 may be in a molar ratio of about 4 to about 5.

In embodiments, the compressor 102 may maintain a partial vacuum in the pyrolysis assembly 106. Byproducts from the pyrolysis assembly 106—such as acetylene, ethylene and benzene—are delivered, along with the hydrogen, via the compressor 102 and to the Sabatier reactor 103. Under Sabatier conditions, these byproducts can be reduced to corresponding saturated alkanes, which become part of the feed to the pyrolysis assembly 106. Such alkanes can react to form carbon and hydrogen more rapidly than methane, so they can increase the output of carbon and hydrogen.

Viewed as a unit, the combination of the Sabatier reactor 103, the methane pyrolysis assembly 106, and the OGA 105 provide the following:

In embodiments, methane pyrolysis can work well at temperatures>1100° C., and is endothermic. This can require about 450 W of power (assuming 1.5 kg/day methane flow). Since the Sabatier reactor 103 operates exothermically at 400° C., it can be used to pre-heat the methane for the pyrolysis assembly 106. This might be accomplished by completing the water recovery from the Sabatier reactor 103 at this temperature using a zeolite membrane, as noted above, or by inserting a heat exchanger to recover this heat.

Examples

Figure 4A:
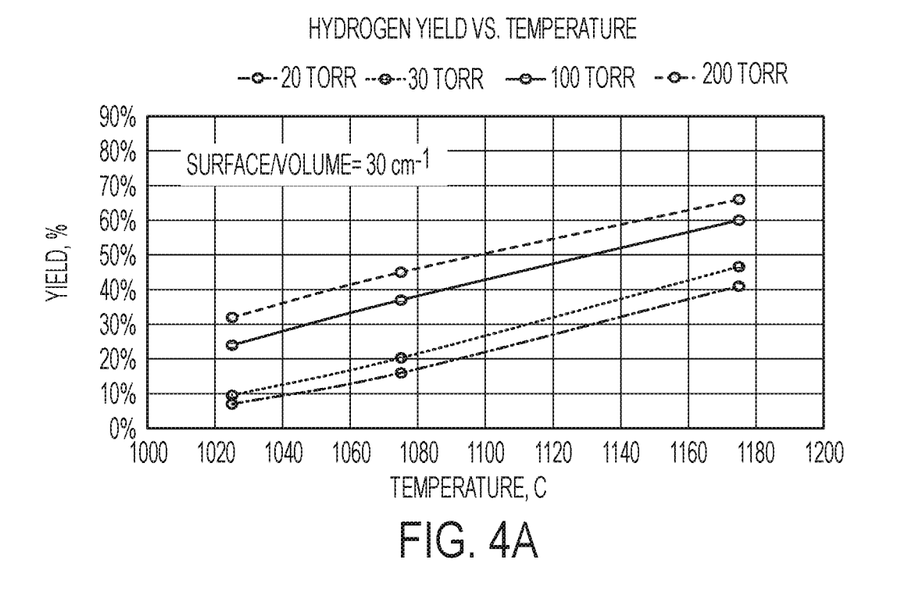
FIGS. 4A-B are plots of hydrogen yield versus temperature according to embodiments of the present invention.
Figure 4B:
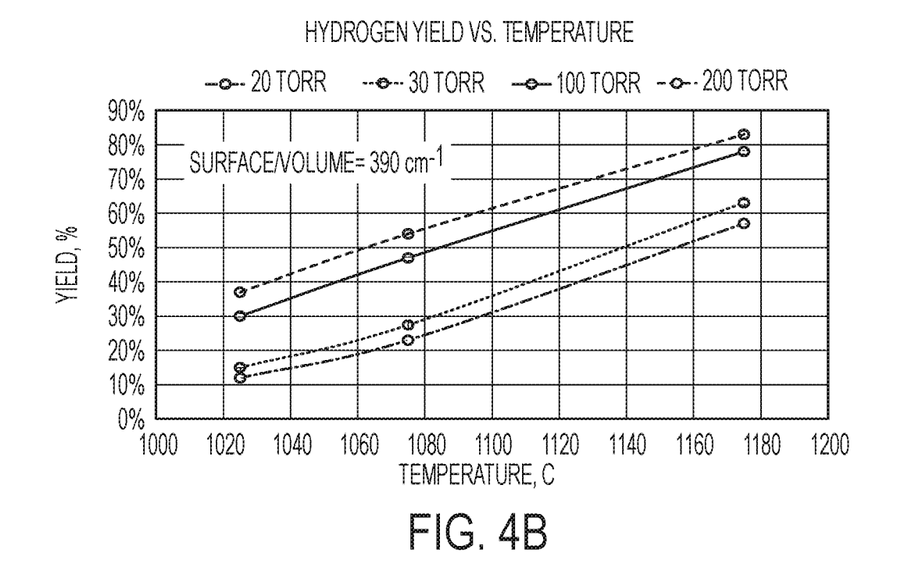

FIGS. 4A-B are plots of hydrogen yield versus temperature according to embodiments of the present invention. For this computer model study, methane was assumed to be the only feed component. FIGS. 4A-B shows that the hydrogen yield is a function of the pyrolysis reaction temperature, pyrolysis pressure, and the surface area/volume ratio for the pre-form. Relatively high conversion can be obtained by increasing the pressure, increasing temperature, or using a pre-form with higher surface/volume ratio.

Figure 5A:
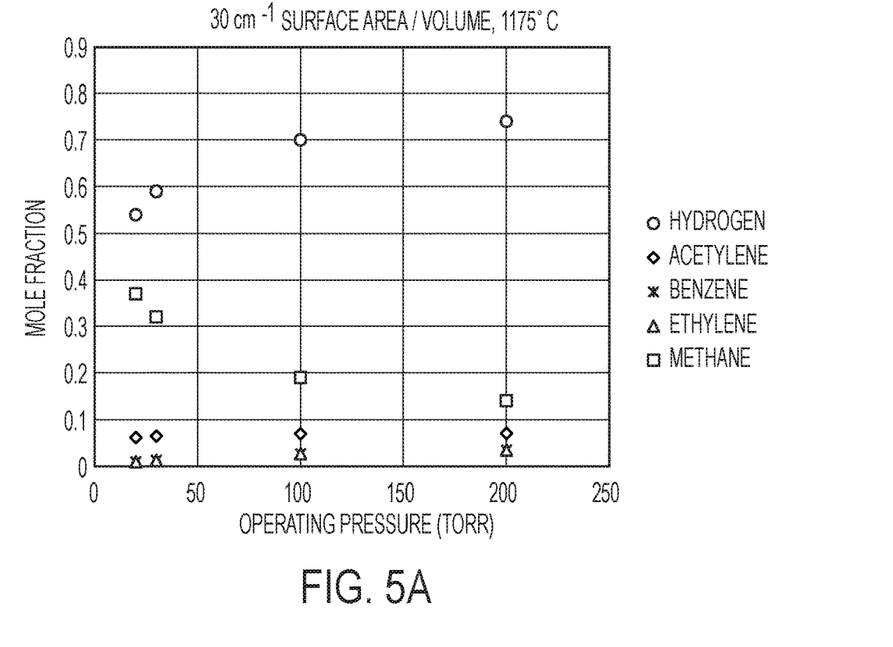
FIGS. 5A-B are plots of mole fraction yield versus pressure according to embodiments of the present invention.
Figure 5B:
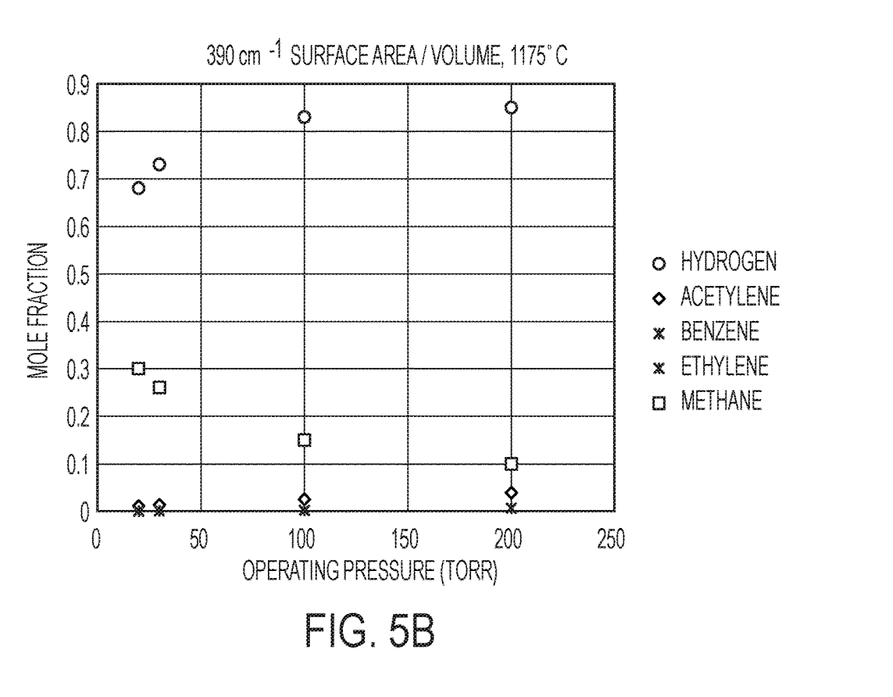

FIGS. 5A-B are plots of mole fraction yield versus pressure according to embodiments of the present invention. For this computer model study, methane was assumed to be the only feed component. FIGS. 5A-B show that the hydrogen yield is a function of the pyrolysis reaction pressure, and the surface area/volume ratio for the pre-form. Relatively high conversion can be obtained by increasing the pressure or using a higher density pre-form.

Figure 6A:
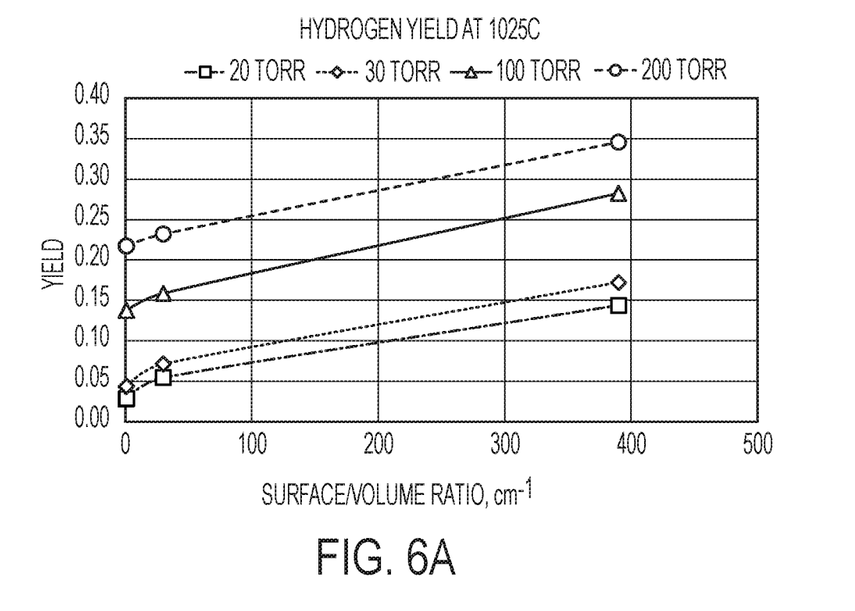
FIGS. 6A-C are plots of hydrogen yield versus surface/volume pre-form ratio according to embodiments of the present invention.
Figure 6B:
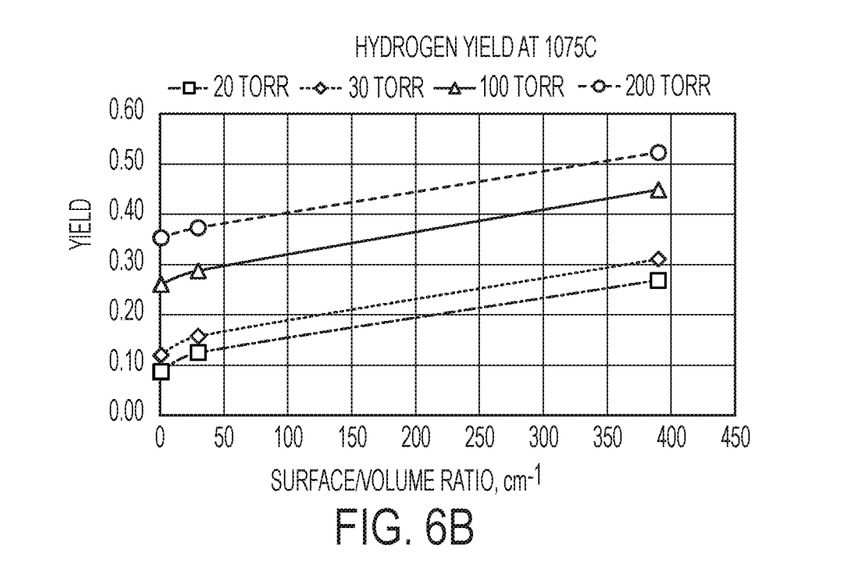
Figure 6C:
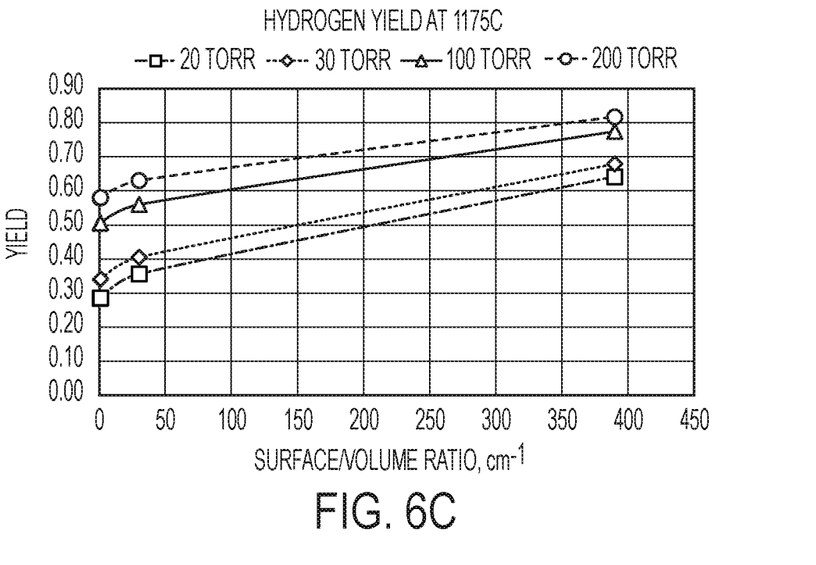
Figure 7A:
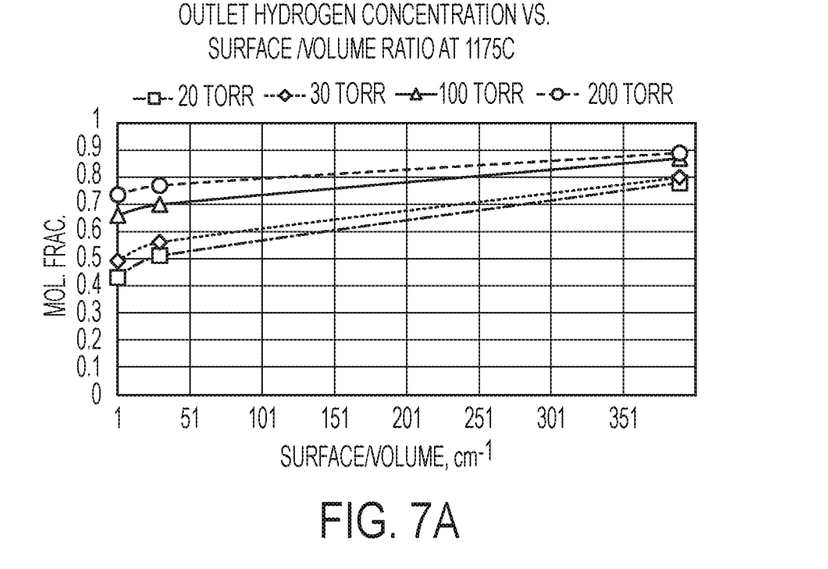
FIGS. 7A-D are plots of hydrogen, methane, acetylene, and benzene mole fraction yields versus surface/volume pre-form ratio, according to embodiments of the present invention.
Figure 7B:
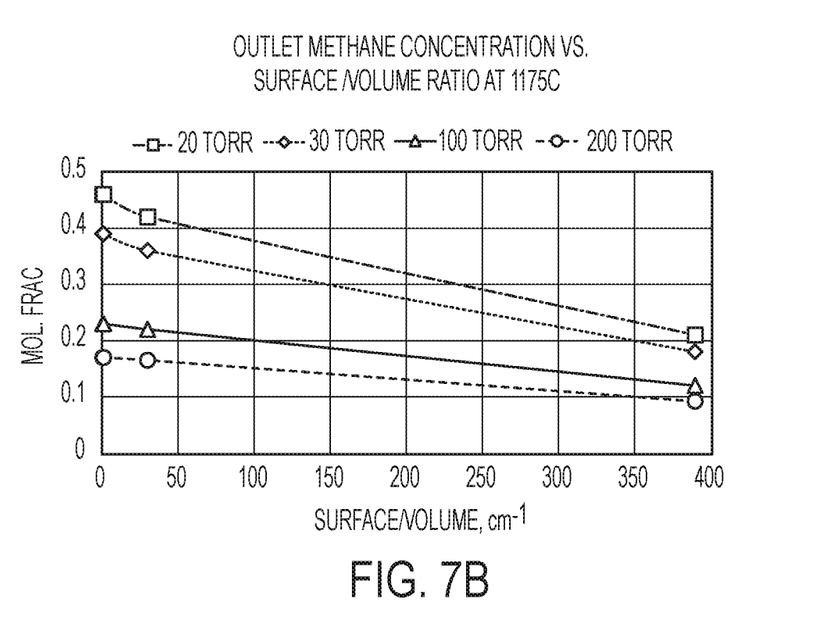
Figure 7C:
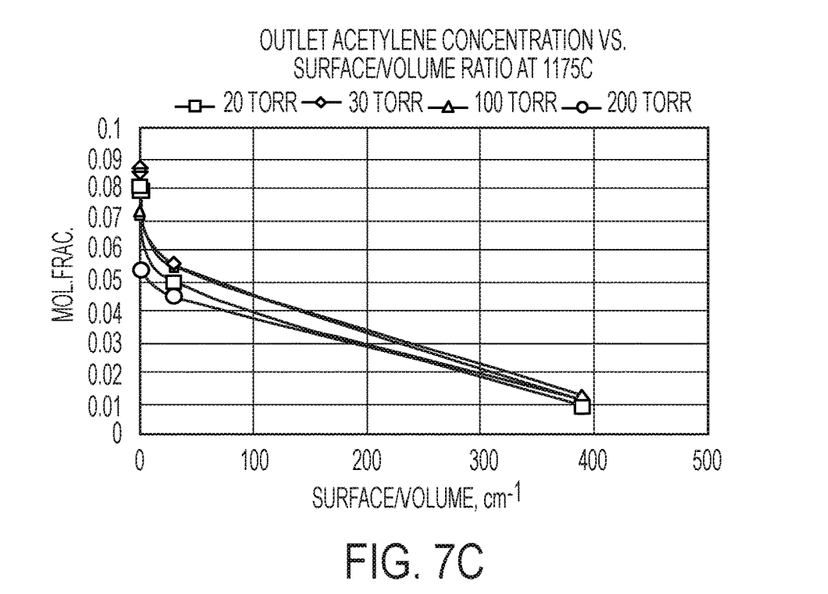
Figure 7D:
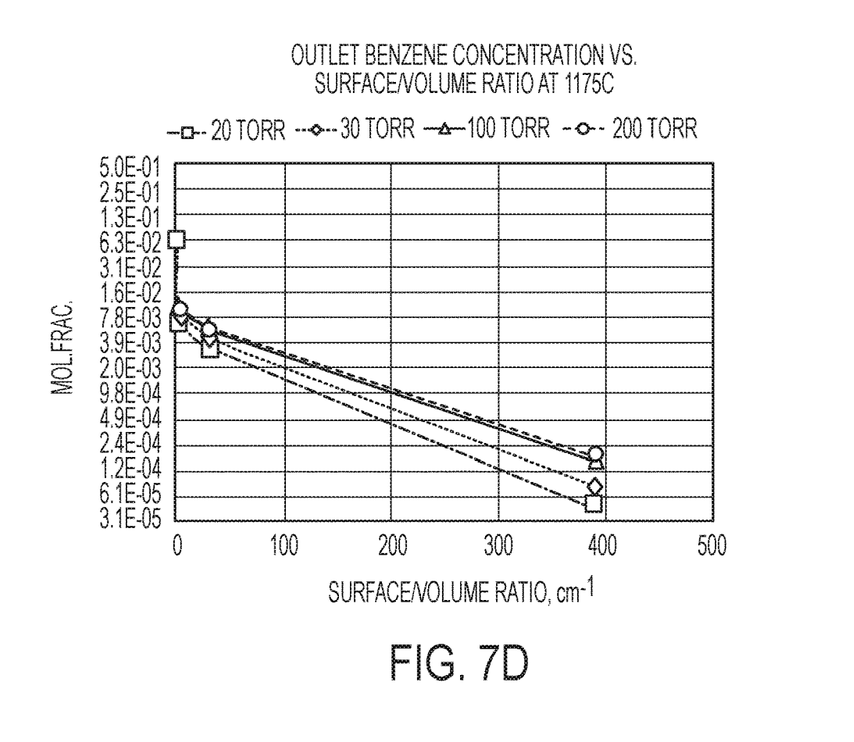

FIGS. 6A-C are plots of hydrogen yield versus surface/volume pre-form ratio according to embodiments of the present invention. For this computer model study, methane was assumed to be the only feed component. FIGS. 6A-C show that the hydrogen yield is a function of the pyrolysis reaction temperature, pyrolysis reaction pressure, and the surface area/volume ratio for the pre-form. Relatively high conversion can be obtained by increasing the temperature, pressure or using a higher density pre-form.

FIGS. 7A-D are plots of hydrogen, methane, acetylene, and benzene mole fraction yields versus surface/volume pre-form ratio, according to embodiments of the present invention. For this computer model study, methane was assumed to be the only feed component. FIGS. 7A-D show that the hydrogen, methane, acetylene, and benzene yields are functions of the pyrolysis reaction temperature, pyrolysis reaction pressure, and the surface area/volume ratio for the pre-form. Relatively high conversion can be obtained by increasing the pressure or using a pre-form with higher surface area/volume ratio.

It is evident from these plots that increasing the surface area/volume ratio changes the carbon-containing product distribution. Facilitating carbon deposition in the pre-forms also has the advantage of reducing the gas phase concentrations of heavier hydrocarbons which might nucleate to form soot particles. Soot generation in a manned space vessel is particularly harmful. Note also from FIGS. 7C-D that in the extreme of low surface area/volume the concentrations of acetylene and benzene increase significantly. This is also true for other hydrocarbons, not included in the plots. While the Sabatier reactor will reduce these and return them to the methane pyrolysis reactor, generating these compounds reflects an inefficiency in the process. These are also toxic materials and have the potential to make tarry materials which might be difficult to handle. There is a clear benefit in increasing the surface area/volume ratio. A desired surface area/volume may be greater than 20 $cm^{-1}$.

It should be understood, of course, that the foregoing relates to exemplary embodiments of the invention and that modifications may be made without departing from the spirit and scope of the invention as set forth in the following claims.

We claim:

1. An environmental control system, comprising:
a carbon dioxide source;
a compressor downstream of the carbon dioxide source;
a Sabatier reactor downstream of the compressor, wherein the Sabatier reactor produces methane and water;
a water separator downstream of the Sabatier reactor, wherein the water separator produces methane and water;
a pyrolysis assembly downstream of the water separator and upstream of the compressor, wherein the pyrolysis assembly includes a pre-form that adheres carbon and has a surface area/volume ratio of at least 20 $cm^{-1}$, wherein the pyrolysis assembly produces hydrogen;
an oxygen generating assembly (OGA) directly downstream of the water separator, wherein the OGA produces hydrogen and oxygen; and
wherein hydrogen produced from the OGA mixes with carbon dioxide exiting the compressor and before the exiting carbon dioxide enters the Sabatier reactor.

2. The system of claim 1, wherein the compressor receives hydrogen from the pyrolysis assembly.

3. The system of claim 1, wherein the Sabatier reactor receives carbon dioxide from the carbon dioxide source and receives hydrogen from the OGA.

4. The system of claim 1, wherein the pyrolysis assembly receives methane from the water separator.

5. The system of claim 1, wherein the carbon dioxide source is a Carbon Dioxide Removal Assembly (CDRA).

6. The system of claim 1, wherein the system is in a gravity free environment.

7. The system of claim 1, wherein the system is in a deep space vehicle.

8. An environmental control system, comprising:
a carbon dioxide source;
a compressor downstream of the carbon dioxide source;
a Sabatier reactor downstream of the compressor, wherein the Sabatier reactor reacts carbon dioxide with hydrogen;
a water separator downstream of the Sabatier reactor, wherein the water separator separates hydrocarbons from water, wherein the hydrocarbons include methane and ethane;
a pyrolysis assembly downstream of the water separator and upstream of the compressor, wherein the pyrolysis assembly includes a pre-form that adheres carbon, wherein the pyrolysis assembly pyrolyzes methane;
an oxygen generating assembly (OGA) directly downstream of the water separator, wherein the OGA electrolyzes water;
wherein hydrogen produced from the OGA mixes with carbon dioxide exiting the compressor and before the exiting carbon dioxide enters the Sabatier reactor.

9. The system of claim 8, wherein the pre-form comprises carbon fibers.

10. The system of claim 9, wherein the carbon fibers are tightly configured into criss-crossed layers.

11. The system of claim 9, wherein the carbon fibers are loosely and randomly arranged.

12. The system of claim 9, wherein the pre-form includes alternating tight regions and loose regions of carbon fibers.

13. The system of claim 8, wherein the Sabatier reactor produces methane and water.

14. The system of claim 8, wherein the pyrolysis assembly produces carbon, hydrogen, acetylene, and benzene.

15. An environmental control system, comprising:
a carbon dioxide source;
a compressor downstream of the carbon dioxide source;
a Sabatier reactor downstream of the compressor, wherein the Sabatier reactor reacts carbon dioxide with hydrogen to produce methane and water;
a water separator downstream of the Sabatier reactor, wherein the water separator separates hydrocarbons from water, wherein the hydrocarbons include methane;
a pyrolysis assembly downstream of the water separator and upstream of the compressor, wherein the pyrolysis assembly pyrolyzes methane to produce carbon and hydrogen, wherein the pyrolysis assembly includes a pre-form that adheres carbon;
an oxygen generating assembly (OGA) directly downstream of the water separator, wherein the OGA electrolyzes water to hydrogen and oxygen;
wherein hydrogen produced from the OGA mixes with carbon dioxide exiting the compressor and before the exiting carbon dioxide enters the Sabatier reactor.

16. The system of claim 15, wherein the Sabatier reactor operates at 400° C. and 1 atm.

17. The system of claim 15, wherein the pyrolysis assembly operates at 1100° C. and 20-100 torr.

18. The system of claim 15, wherein the pre-form is removable from the pyrolysis assembly once the pre-form is loaded with carbon.

19. The system of claim 15, wherein oxygen produced by the OGA is routed to an environment for occupants.

* * * * *